United States Patent

Staab et al.

[11] 4,298,751
[45] Nov. 3, 1981

[54] CYCLICALLY SUBSTITUTED FULVALENOPHANES

[75] Inventors: Heinz Staab, Heidelberg; Joachim Ippen, Cologne, both of Fed. Rep. of Germany

[73] Assignee: Basf Aktiengesellschaft, Ludwigshafen, Fed. Rep. of Germany

[21] Appl. No.: 176,402

[22] Filed: Aug. 8, 1980

[30] Foreign Application Priority Data

Sep. 14, 1979 [DE] Fed. Rep. of Germany ....... 2937225

[51] Int. Cl.³ .................. C07D 495/02; C07D 495/22
[52] U.S. Cl. .................. 549/11; 260/239 R; 260/239.3 P; 260/330; 260/330.3; 260/333; 260/338; 260/340.2; 260/343; 260/343.41; 549/10
[58] Field of Search .............. 260/239 R, 239.3 P, 260/330, 330.3, 333, 338, 340.2, 343, 343.41; 549/10, 11

[56] References Cited

FOREIGN PATENT DOCUMENTS 2364445 12/1972 Fed. Rep. of Germany ........ 549/35

OTHER PUBLICATIONS

Narita et al., International Journal of Methods in Synthetic Organic Chemistry, No. 8, (1976), pp. 489–514.

Primary Examiner—Richard Raymond
Attorney, Agent, or Firm—John H. Shurtleff

[57] ABSTRACT

Cyclically substituted fulvalenophanes of the formula

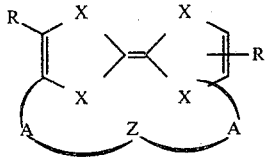

where X is S, Se or Te, R is H or lower alkyl, A is —$(CH_2)_n$— and Z is a radical of the formula

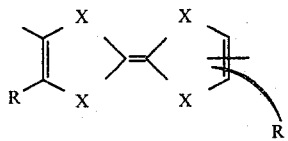

a p-phenylene radical or a quinodimethane radical of the formula

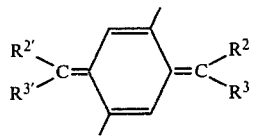

where the radicals $R^2$ and $R^3$ are halogen, carboxylic acid ester groups or cyano and $R^3$ may also be hydrogen, and the quinodimethane ring may be substituted by halogen, nitro or cyano.

3 Claims, No Drawings

CYCLICALLY SUBSTITUTED FULVALENOPHANES

The present invention relates to novel cyclically substituted fulvalenophanes, to a process for their preparation and to their use.

The novel fulvalenophanes according to the invention are interesting organic conductors or semi-conductors or intermediates in the preparation of such materials. They have the formula

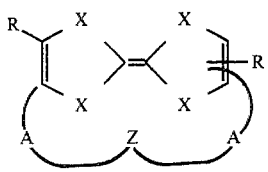

where X is S, Se or Te, R is H or lower alkyl, A is —$(CH_2)_n$—, where n is 2, 3, 4, or 5 and one or more of the —$CH_2$— members may be replaced by —S—, —$SO_2$—, —O—, —NH—, —$NR^1$—, —CO—, —O—CO—, —O—CO—O— or —$NR^1$—CO—, $R^1$ being alkyl of 1 to 5 carbon atoms, and Z is a radical of the formula

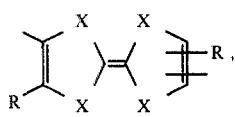

p-phenylene, which may substituted by halogen, nitro or cyano, or a radical of the formula

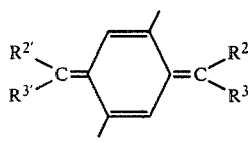

where $R^2$ and $R^3$ are halogen, carboxylic acid ester groups or cyano and $R^3$ may also be hydrogen, and the quinodimethane ring may be substituted by halogen, nitro or cyano. Lower alkyl R is, for example, alkyl of 1 to 5 carbon atoms, preferably methyl.

Examples of compounds of industrial interest are the tetrathiofulvalenes of the formula

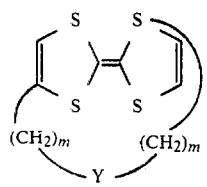

where m is 2, 3, 4 or 5 and Y is one of the radicals

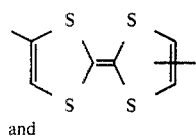

and

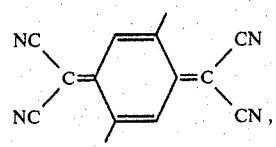

or is p-phenylene which may contain cyano, nitro or halogen substituents.

More specific examples are the tetrathiofulvalenophanes of the formula

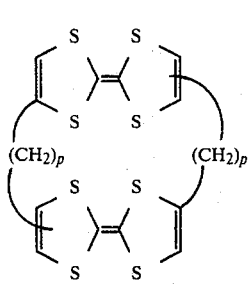

where p is 2, 3 or 4, or of the formula

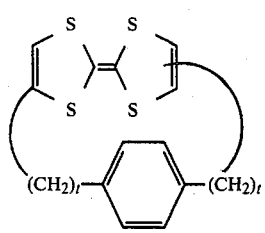

where t is 3, 4 or 5.

The novel cyclically substituted fulvalenophanes are prepared by conventional methods, wherein a compound of the formula

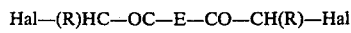

Hal—(R)HC—OC—E—CO—CH(R)—Hal      V where Hal is chlorine or bromine and E is —$(CH_2)_n$— or —A—Z—A—, (a) is converted, by reaction with a compound of the formula

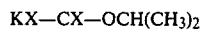

KX—CX—OCH(CH_3)_2      VI into a compound of the formula

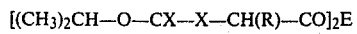

[(CH_3)_2CH—O—CX—X—CH(R)—CO]_2E      VII, (b) the compound of the formula VII is cyclized by treatment with an acid, to give a compound of the formula

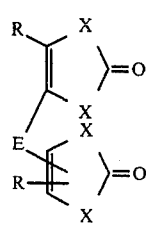

(c) the compound of the formula VIII is treated with phosphorus(V) sulfide to give the compound of the formula

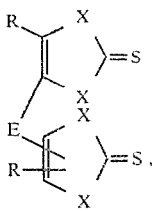

IX (d) the compound of the formula IX is converted to the compound of the formula

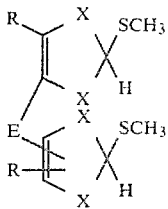

X by methylation and reduction, (e) the compound of the formula X is converted to the tetrafluoborate of the formula

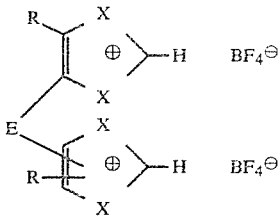

XI by treatment with fluoboric acid and (f) the fluoborate of the formula XI is treated with a tertiary amine.

The starting material of the formula V may be obtained, for example, by reacting an acid chloride of the formula Cl—OC—E—CO—Cl with diazomethane and then treating the bis-diazo compound with a hydrogen halide.

In step (a) the bis-(haloketone) of the formula V is reacted with a compound of the formula VI, eg. potassium O-isopropyl-dithiocarbonate (KS—C-S—O—CH(CH$_3$)$_2$), in a solvent, for example acetone, at from 20° to 55° C.

The cyclization of the compound of the formula VII in step (b) is carried out with an acid, eg. with concentrated sulfuric acid or with 70% strength perchloric acid, at 20°-50° C.

In step (c), the compound of the formula VIII is reacted with phosphorus(V) sulfide, advantageously in xylene at from 120° to 140° C.

In step (d), the compound of the formula IX is methylated, advantageously by means of methyl iodide in nitromethane at 50°-80° C., and the reaction product thereby obtained is reduced—advantageously without prior isolation—for example with sodium borohydride. This reduction, which gives the compound of the formula X, is carried out, for example, at from −78° to +50° C., in a mixture of tetrahydrofuran and methanol.

The fluoborate of the formula XI is obtained from the compound of the formula X, in step (e), by reaction with fluoboric acid, for example in acetic anhydride at from 0° to 30° C. Finally, in step (f), the fluoborate of the formula XI is cyclized by treatment with a tertiary amine. This reaction is effected, for example, by adding a solution of triethylamine in acetonitrile dropwise at from 0° to 40° C. to a solution of the fluoborate in acetonitrile.

The novel fulvalenophanes are organic conductors, photoconductors or semi-conductors.

According to a further feature of the invention, the novel fulvalenophanes can be used for the preparation of further organic conductors, photoconductors or semiconductors by treating them with compounds of the formula

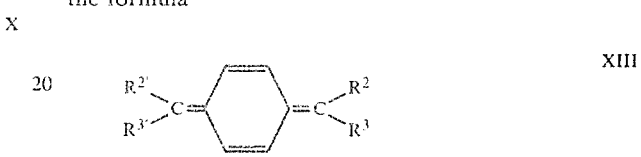

XIII where $R^2$ and $R^3$ are halogen, carboxylic acid ester groups or cyano and $R^3$ may also be hydrogen, and the quinodimethane ring may be substituted by halogen, nitro or cyano, or with substituted benzenes, eg. tetracyanobenzene.

This reaction, which is carried out, for example, at from 0° to 50° C. in a mixture of acetonitrile and carbon disulfide, gives complex compounds which, for example, contain from 1 to 4 moles of the quinodimethane compound of the formula XIII or of the benzene compound per mole of fulvalenophane.

EXAMPLE 1

Preparation of [2,2]-tetrathiafulvalenophane of the formula III 1,6-bis-Diazo-2,5-dioxohexane A solution of 9.7 g (62.5 millimoles) of succinic acid dichloride in 100 ml of ether is slowly added dropwise to 600 ml (0.5 mole) of a diazomethane solution, whilst stirring and cooling with ice. The mixture is stirred for a further 3 hours whilst being cooled with ice, and is then left to stand overnight at room temperature. It is then decanted and the excess diazomethane and a part of the ether is blown off. The solution is decanted from a brown residue and when a volume of about 300 ml has been reached, is employed, without additional purification, for the next step.

1,6-Dichloro-2,5-dioxohexane

A solution of about 62 millimoles of 1,6-bis-diazo-2,5-dioxohexane in ether is slowly added dropwise to 300 ml of a saturated solution of hydrogen chloride gas in ether, whilst stirring and cooling with ice. Gas is evolved and the mixture turns cloudy. It is stirred for a further 3 hours at room temperature and then left to stand overnight. Thereafter, the solution is concentrated on a rotary evaporator, leaving a crystalline substance and a small amount of oil. 20 ml of ethanol are added and the white crystalline product is filtered off. Recrystallization from cyclohexane gives colorless flakes which melt at 87°-88° C. The yield is 2.6 g of 1,6-dichloro-2,5-dioxohexane (23%).

2,15-Dimethyl-3,14-dioxa-7,10-dioxo-5,12-dithia-4,13-dithioxohexadecane (see formula VII, with R=H, X=S and E=—(CH$_2$)$_2$—)

1.7 g (9.28 millimoles) of 1,6-dichloro-2,5-dioxohexane are dissolved in 50 ml of acetone and 3.2 g (18.5 millimoles) of potassium isopropylxanthate are added at room temperature. A colorless pasty precipitate forms immediately. The mixture is stirred for a further 3 hours at room temperature and is then poured into 200 ml of water, and the batch is extracted with methylene chloride. The methylene chloride phase is dried and concentrated. Pale brown crystals are obtained and these are recrystallized from carbon tetrachloride. The yield is 3 g of 2,15-dimethyl-3,14-dioxa-7,10-dioxo-5,12-dithia-4,13-dithioxohexadecane (84%). Melting point: 82°-83° C.

1,2-bis-(Isodithionyl)-ethane (see formula VIII, with R=H, X=S and E=—(CH$_2$)$_2$—)

3 g (7.8 millimoles) of 2,15-dimethyl-3,14-dioxa-7,10-dioxo-5,12-dithia-4,13-dithioxohexadecane are introduced slowly, in small portions, into 20 ml of concentrated sulfuric acid, whilst cooling with ice. The mixture is then stirred for 2 hours at room temperature, after which the dark brown solution is poured into ice water. The colorless suspension is extracted with ether. The ether phase is washed with water, dried over sodium sulfate and concentrated. White crystals are obtained, and these are purified on a silica gel column, using methylene chloride as the mobile phase. After recrystallization from toluene, 1,2-bis-(isodithionyl)-ethane is obtained in the form of long white needles of melting point 135°-136° C. The yield is 1.8 g (87%).

1,2-bis-(Isotrithionyl)-ethane (see formula IX, with R=H, X=S and E=—(CH$_2$)$_2$—)

1.8 g (6.8 millimoles) of 1,2-bis-(isodithionyl)-ethane and 1.5 g of phosphorus pentasulfide in 50 ml of xylene are refluxed for 6 hours. When the mixture has cooled, the solvent is filtered off and the residue is repeatedly extracted by boiling with toluene. The combined solvent extracts are concentrated, leaving an orange crystalline substance. This product is recrystallized 3 times from toluene. The yield of 1,2-bis-(isotrithionyl)-ethane is 1.6 g (80%). The melting point is 172°-174° C.

1,2-bis-(2'-Methylthio-1',3'-dithiol-4'-yl)-ethane (see formula X, with E=—(CH$_2$)$_2$—, R=H and X=S)

A suspension of 205.8 mg (0.7 millimole) of 1,2-bis-(isotrithionyl)-ethane in 3 ml of nitromethane and 2 ml of methyl iodide is stirred for 2.5 hours at 55° C. and then overnight at room temperature. Thin layer chromatography is used to check whether the reaction is complete. The solvent is blown off with argon and the yellow residue is dried under reduced pressure from an oil pump. The bis-sulfonium iodide thus obtained (crude yield 403 mg, ie. 100%) is hydrogenated, without further purification, as follows:

403 mg (0.7 millimole) of bis-sulfonium iodide are suspended in 4 ml of absolute tetrahydrofuran and 4 ml of absolute methanol and the suspension is cooled to −78° C. 262 mg (7 millimoles) of sodium borohydride are added in small portions and stirring is continued for 3 hours at −78° C. The temperature is then allowed to rise from −78° C. to +10° C. over 2.5 hours, during which the reaction mixture froths copiously. The yellow suspension is then poured into 100 ml of ether and the mixture is washed with 100 ml of water. The aqueous phase is washed with 100 ml of ether and the two ether phases are washed twice with water and once with saturated sodium chloride solution. The combined ether phases are then dried over sodium sulfate and concentrated. A yellow oil is obtained and this is filtered over a silica gel column (length 30 cm, diameter 1 cm) under an argon atmosphere, using a 2:1 mixture of methylene chloride and carbon tetrachloride as the mobile phase. The eluate is concentrated, leaving the product of the formula X as a yellow sensitive oil. The yield is from 27 to 40%.

bis-Dithiolium ion (see formula XI, with R=H, E=—(CH$_2$)$_2$— and X=S)

300 mg (0.92 millimole) of 1,2-bis-(2'-methylthio-1',3'-dithiol-4'-yl)-ethane in 6.5 ml of acetic anhydride are introduced into a reaction vessel, under nitrogen, and cooled to 0° C. 0.9 ml of fluoboric acid is then added dropwise in the course of 15 minutes. A brown solution is obtained, which is stirred for 40 minutes at 0° C. During this time, a small amount of pale brown precipitate forms. 50 ml of absolute ether are added, whereupon a further quantity of brown precipitate is formed. After briefly stirring the mixture, the ether is pipetted off and the precipitate is washed 5 more times in the same manner. Thereafter, the pale brown precipitate is dried under reduced pressure from an oil pump, and is then employed, without additional purification, in the next step.

[2,2]-Tetrathiafulvalenophane

A solution of 0.92 millimole of bis-dithiolium fluoborate in 30 ml of absolute acetonitrile is added dropwise to a solution of 3 ml of triethylamine in 50 ml of absolute acetonitrile under an argon atmosphere, at room temperature. The addition requires 45 minutes, after which the mixture is stirred for 1 hour at room temperature and then filtered under argon. The orange solution obtained is concentrated on a rotary evaporator and the residue is dried under reduced pressure from an oil pump. Fractional recrystallization of the product from carbon disulfide gives a yield of 10-15% of [2,2]-tetrathiafulvalenophane in the form of yellow crystals which turn black at 210° C. and do not melt up to 310° C.

EXAMPLE 2

Preparation of [3,3]-tetrathiafulvalenophane of the formula III

1,7-bis-Diazo-2,6-dioxoheptane 600 ml (0.5 mole) of a diazomethane solution are introduced into an Erlenmeyer flask. A solution of 16.9 g (0.1 mole) of glutaric acid dichloride in 200 ml of ether is then slowly added dropwise whilst stirring and cooling with ice. Thereafter the mixture is stirred for 3 hours whilst cooling with ice, and is then left to stand overnight at room temperature. The excess diazomethane and a portion of the ether are blown off by means of compressed air behind the screen of a well-ventilated fume cupboard. When the solution has reached a volume of about 300 ml, the product is employed, without purification, in the next step.

1,7-Dichloro-2,6-dioxoheptane

A solution of about 100 millimoles of 1,7-bis-diazo-2,6-dioxoheptane in 300 ml of ether is added dropwise to 300 ml of a saturated solution of gaseous hydrogen chloride in ether, whilst stirring and cooling with ice. The mixture turns cloudy and gas is evolved. It is stirred for 2 hours at room temperature and then left to stand overnight. The colorless product which has precipitated is filtered off and washed with ether. The melting point of the product—which is obtained in varying amounts—is 74°–75° C.

Water is cautiously added to the ether phase and the pH is brought to 6 with sodium bicarbonate. The ether phase is separated off and dried by means of sodium sulfate. It is concentrated, leaving a colorless oil which after cooling to 0° C. crystallizes throughout. Recrystallization from cyclohexane gives 1,7-dichloro-2,6-dioxoheptane in the form of colorless needles which melt at 74°–75° C. The total yield is 11 g (43%).

2,16-Dimethyl-3,15-dioxa-7,11-dioxo-5,13-dithia-4,14-dithioxoheptadecane (see formula VII, with R=H, X=S and E=—(CH$_2$)$_3$—)

3.8 g (14 millimoles) of 1,7-dichloro-2,6-dioxoheptane are introduced into 75 ml of acetone and 4.8 g (28 millimoles) of potassium isopropylxanthate are added at room temperature. A colorless pasty precipitate forms immediately. The mixture is stirred for 2 hours at room temperature and is then poured into 200 ml of water and extracted with ether. The ether phase is dried and concentrated. Colorless crystals are obtained and these are recrystallized from carbon tetrachloride. The yield of 2,16-dimethyl-3,15-dioxa-7,11-dioxo-5,13-dithia-4,14-dithioxoheptadecane is 4.3 g (74%) and the melting point is 98°–100° C.

1,3-bis-(Isodithionyl)-propane (see formula VIII, with R=H, X=S and E=—(CH$_2$)$_3$—)

1.4 g (3.5 millimoles) of 2,16-dimethyl-3,15-dioxa-7,11-dioxo-5,13-dithia-4,14-dithioxoheptadecane are introduced very slowly, in small portions, into 3 ml of concentrated sulfuric acid, whilst cooling with ice. The dark brown mixture is stirred for one hour at 0° C. and is then poured into ice water. A colorless emulsion is formed, which is extracted by shaking with ether. The ether phase is dried over sodium sulfate and concentrated and the residue is recrystallized from cyclohexane. The yield is 913 mg of 1,3-bis-(isodithionyl)-propane (93%) and the melting point of the colorless product is 63°–64° C.

1,3-bis-(Isotrithionyl)-propane (see formula IX, with R=H, X=S and E=—(CH$_2$)$_3$—)

1.3 g (4.7 millimoles) of 1,3-bis-(isodithionyl)-propane and 1 g of phosphorus pentasulfide (P$_4$S$_{10}$) in 50 ml of xylene are refluxed for 2.5 hours. When the mixture has cooled, the solvent is decanted and concentrated. The residue is repeatedly extracted by boiling with toluene, and the toluene phase is concentrated. The combined reddish yellow residues are filtered over a silica gel column, using methylene chloride. A yellow fraction is obtained, which is concentrated and charged onto a second, short silica gel column (length 15 cm, diameter 5 cm); in this case, the mobile phase used is a 7:3 mixture of chloroform and carbon tetrachloride. The product crystallizes out on the column and migrates very slowly. After chromatographic separation, the product is recrystallized from toluene. Yield of 1,3-bis-(isotrithionyl)-propane: 750 mg (52%). The melting point is 101°–102° C.

1,3-bis-(2'-Methylthio-1',3'-dithiol-4'-yl)-propane (see formula X, with R=H, X=S and E=—(CH$_2$)$_3$—)

A suspension of 1.23 g (4 millimoles) of 1,3-bis-isotrithionyl)-propane in 11 ml of nitromethane and 4 ml of methyl iodide is refluxed for 2.5 hours. After about 30 minutes, a yellow precipitate forms. The mixture is allowed to cool, a further 2 ml of methyl iodide are added, and the whole is stirred overnight at room temperature. The solvent is then blown off with nitrogen and the orange yellow residue is dried under reduced pressure from an oil pump. The bis-sulfonium iodide thus obtained (crude yield: 2.36 g (100%)) is hydrogenated as follows, without additional purification:

2.36 g=4 millimoles of the crude bis-sulfonium iodide are suspended in 21.5 ml of absolute tetrahydrofuran and 21.5 ml of absolute methanol and the suspension is cooled to −78° C. 1.5 g (40 millimoles) of sodium borohydride are added in 3 portions and the mixture is then stirred for 3 hours at −78° C. The temperature is allowed to rise to −20° C. over 1.5 hours, during which the reaction mixture froths copiously. The yellow mixture is then poured into 200 ml of ether and the batch is washed with 200 ml of water. A yellow substance remains undissolved between the two phases. The aqueous phase is twice extracted with 100 ml of ether. The combined ether phases are washed twice with 100 ml of water and once with 100 ml of a saturated sodium chloride solution, dried over sodium sulfate and filtered. The ether solution is then concentrated and the deep yellow residue is filtered over a silica gel column (length 30 cm, diameter 1 cm) under a nitrogen atmosphere, with methylene chloride as the mobile phase. The filtrate is concentrated and the product is left in the form of a yellow sensitive oil. The yield is 1.044 g (77%).

bis-Dithiolium ion (see formula XI, with R=H, E=—(CH$_2$)$_3$— and X=S)

1.044 g (3.06 millimoles) of 1,3-bis-(2'-methylthio-1',3'-dithiol-4'-yl)-propane in 21 ml of acetic anhydride are introduced into a reaction vessel under nitrogen, and cooled to 0° C. 2.91 ml of fluoboric acid are then added dropwise over 15 minutes. A brown solution is obtained, which is stirred for 40 minutes at 0° C. During this time, a small amount of pale brown precipitate forms. 200 ml of absolute ether are added, whereupon a dark brown product precipitates. After briefly stirring the mixture, the ether is pipetted off and the precipitate is washed similarly four more times, in each case using 100 ml of ether. The remaining ether is blown off with nitrogen and the product is dried under reduced pressure from an oil pump. The reddish brown precipitate is employed, without additional purification, in the next step.

[3,3]-Tetrathiafulvalenophane

A solution of the crude bis-dithiolium fluoborate in 90 ml of absolute acetonitrile is slowly added dropwise at room temperature, under a nitrogen atmosphere, to a solution of 3.5 ml of triethylamine in 35 ml of absolute acetonitrile. The mixture is stirred for 40 minutes and is then concentrated on a rotary evaporator. After having been dried under reduced pressure from an oil pump, the reddish brown residue is repeatedly digested with carbon disulfide. The carbon disulfide solution is concentrated, leaving a residue in a crude yield of 130 mg (9%). The NMR spectrum shows the presence of a main product, and possibly of isomers. For further purification, the [3,3]-tetrathiafulvalenophane is recrystallized from carbon disulfide.

EXAMPLE 3

Preparation of [3]-tetrathiafulvaleno[3]paracyclophane (see formula IV)

p-Phenylene-γ,γ-dibutyryl chloride 2.5 g (10 millimoles) of p-phenylene-γ,γ-dibutyric acid in 34 ml of thionyl chloride are refluxed for 2 hours. During the reaction, the solution turns dark brown. When the mixture has cooled, the thionyl chloride is distilled off and the oil which remains is mixed with 30 ml of petroleum ether. The acid chloride dissolves, whilst decomposition products remain undissolved in the form of a tarry residue. The solution is clarified with active charcoal, filtered and concentrated. Pale brown crystals are formed, which are mixed with a small amount of cyclohexane and then filtered off. Colorless crystals of melting point 49°–55° C. are obtained. The yield of p-phenylene-γ,γ-dibutyryl chloride is 2.38 g (83%).

1,4-bis-(5'-Diazo-4'-oxopentyl)-benzene 600 ml (about 0.5 mole) of diazomethane solution in ether are introduced into an Erlenmeyer flask, fitted with a magnetic stirrer, behind a protective screen. 12 g (42 millimoles) of p-phenylene-γ,γ-dibutyryl chloride dissolved in 200 ml of ether are slowly added dropwise, whilst cooling with ice. Gas is evolved. Stirring is continued for 3 hours and the mixture is then left to stand overnight. The yellow solution is filtered and the ether and excess diazomethane are blown off with compressed air. The solid yellow residue is employed immediately in the next reaction.

1,4-bis-(5'-Chloro-4'-oxopentyl)-benzene

About 42 millimoles of the 1,4-bis-(5'-diazo-4'-oxopentyl)-benzene obtained from the preceding reaction, dissolved in 190 ml of methanol, are slowly added dropwise to a mixture of 117 ml of 5 M sodium chloride solution and 117 ml of 2 N hydrochloric acid solution, with vigorous stirring. The mixture turns cloudy and gas is evolved. Stirring is continued for 30 minutes and the yellow crude product which has precipitated (18.3 g) is filtered off. It is chromatographed over a silica gel column (length 30 cm, diameter 7 cm), using chloroform as the mobile phase, and colorless crystals are obtained; these are recrystallized from isopropanol. 1,4-bis-(5'-Chloro-4'-oxopentyl)-benzene is obtained in 51% yield (6.7 g); melting point 70°–71° C.

1,4-bis-(9'-Methyl-8'-oxa-4'-oxo-6'-thia-7'-thioxo-decanyl)-benzene (see formula VII, with X=S, R=H and

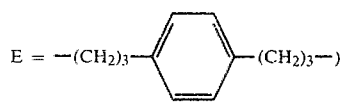

6 g (18 millimoles) of 1,4-bis-(5'-chloro-4'-oxopentyl)-benzene are introduced into 150 ml of acetone and 6.26 g (36 millimoles) of potassium isopropylxanthate are added. The suspension is refluxed for 30 minutes, producing a colorless paste. The acetone is then distilled off and 100 ml of water are added to the residue. An emulsion is obtained, which is extracted with ether. The ether phase is washed with water and then dried over sodium sulfate. Removal of the solvent leaves a pale yellow residue which crystallizes in a refrigerator. The product is chromatographed over a silica gel column (length 30 cm, diameter 3 cm), using methylene chloride as the mobile phase, and is thereby obtained in the form of colorless crystals in a yield of 8.6 g (89%). The melting point is 63°–64° C.

1,4-bis-(3'-Isodithionylpropyl)-benzene (see formula VIII, with R=H, X=S and

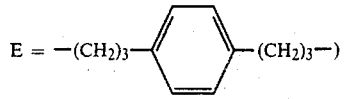

0.5 g (1 millimole) of 1,4-bis-(9'-methyl-8'-oxa-4'-oxo-6'-thia-7'-thioxo-decanyl)-benzene is dissolved in 8 ml of a 1:1 mixture of ether and chloroform. 0.75 ml of perchloric acid is added dropwise very slowly, whilst cooling with ice. After having been stirred for 30 minutes, the mixture is poured into ice water, the organic phase is separated off and the aqueous phase is twice extracted with chloroform. The combined organic phases are dried over sodium sulfate and then concentrated. The resulting oil is filtered over a silica gel column (length 30 cm, diameter 1 cm), using methylene chloride as the mobile phase. 140 mg of 1,4-bis-(3'-isodithionylpropyl)-benzene are obtained in the form of a light brown oil. Since the compound decomposes easily, it is immediately reacted as follows:

1,4-bis-(3'-Isotrithionylpropyl)-benzene (see formula IX with R=H, X=S and

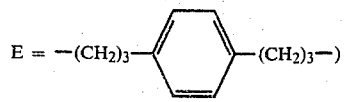

380 mg (0.96 mole) of crude 1,4-bis-(3'-isodithionylpropyl)-benzene are introduced into 15 ml of xylene and 500 mg of phosphorus pentasulfide ($P_4S_{10}$) are added. The mixture is refluxed for 2.5 hours on a bath at 140° C. It is then cooled and filtered, and the reddish brown residue is washed with toluene. The organic phase is concentrated and chromatographed over a silica gel column (length 30 cm, diameter 1 cm) using a 7:3 mixture of carbon tetrachloride and chloroform as the mobile phase. 1,4-bis-(3'-Isotrithionylpropyl)-benzene is obtained in the form of yellow crystals. Yield: 84 mg (27%). Melting point: 99°–100° C.

The overall yield of the last two stages is 5–10% and is independent of the purity of the 1,4-bis-(3'-isodithionylpropyl)-benzene.

1,4-bis-3'-(2''-Methylthio-1'',3''-dithiol-4''-yl)-propyl-benzene (see formula X, with R=H, X=S and

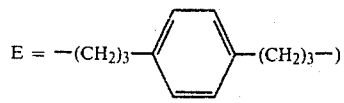

1 g (2.34 millimoles) of 1,4-bis-(3'-isotrithionylpropyl)-benzene in 6.25 ml of distilled nitromethane and 2.5 ml of distilled methyl iodide is refluxed for 2.5 hours on a bath at 70° C. The reddish brown solution is left to cool and 1.2 ml of methyl iodide are added. A yellowish brown precipitate forms. The reaction mixture is stirred overnight, the solvent is then blown off with nitrogen and the yellowish brown crystalline residue is dried under reduced pressure from an oil pump. The crude yield is 1.66 g (100%). The bis-sulfonium iodide obtained is hydrogenated, without further purification, as follows:

1.66 g (2.34 millimoles) of the crude bis-sulfonium iodide are suspended in 13 ml of absolute tetrahydrofuran and 13 ml of absolute methanol and the suspension is cooled to −78° C. 890 mg (23.4 millimoles) of sodium tetrahydridoborate are added in 3 portions and the mixture is stirred for 3 hours at −78° C. It is then allowed to come from −78° C. to −20° C. over a further 3 hours, during which vigorous evolution of gas occurs in the cloudy orange solution. The reaction mixture is poured into ether and washed with water. The aqueous phase is extracted twice with ether and the combined ether phases are then washed twice with 100 ml of water and once with 100 ml of a saturated sodium chloride solution. The organic phase is dried over sodium sulfate and concentrated. A brown oil is obtained, which is chromatographed over a silica gel column (length 30 cm, diameter 1 cm), using methylene chloride as the mobile phase. After concentrating, a pale yellow oil is obtained in a yield of 978 mg (91%). The yield represents the overall yield of the last two steps.

bis-Dithiolium ion (see formula XI, with R=H, X=S and

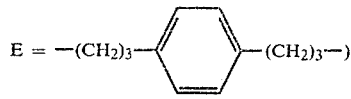

$E = -(CH_2)_3-\langle\rangle-(CH_2)_3-)$ 860 mg (1.89 millimoles) of 1,4-bis-3'-(2''-methylthio-1'',3''-dithiol-4''-yl)-propyl-benzene in 13 ml of acetic anhydride are introduced into a reaction vessel under nitrogen, and cooled to 0° C. 1.8 ml of fluoboric acid are then added dropwise over half an hour. A pale brown solution is obtained which is stirred for 40 minutes at 0° C. During this time, a pale brown precipitate forms. 100 ml of absolute ether are added, resulting in a further amount of precipitate. The mixture is stirred thoroughly and the ether solution is pipetted off after the precipitate has settled out. The precipitate is then washed four more times in this way, using 100 ml of absolute ether at a time. The residual ether is then blown off with nitrogen and the precipitate is dried under reduced pressure from an oil pump. The pale brown product is employed, without further purification, in the next step.

[3]-Tetrathiafulvaleno[3]-paracyclophane

A solution of 1.02 g (1.89 millimoles) of the bis-dithiolium fluoborate from the preceding reaction, in 60 ml of absolute acetonitrile, is added dropwise at room temperature to a solution of 2.2 ml of distilled triethylamine in 22 ml of absolute acetonitrile under a nitrogen atmosphere. The most suitable method is to add the triethylamine solution from a syringe over a period of about half an hour. After the addition, the mixture is stirred for 40 minutes and is then concentrated on a rotary evaporator. The residue is dried under reduced pressure from an oil pump. A reddish brown solid product, consisting mainly of polymers, is obtained. Ether is added in portions of 30 ml and the residue is digested until the ether phase no longer turns yellow. This requires about 300 ml of ether. The combined ether solutions are filtered over a Florisil column (length 30 cm, diameter 1 cm). The column instantly turns green. The yellow ether fraction is concentrated, leaving a yellow substance which crystallizes immediately.

The NMR spectrum shows the presence of the cis- and trans-isomers of [3]-tetrathiafulvaleno[3]paracyclophane in the ratio of about 1:1. The yield of isomer mixture is 195 mg (29%). Trans-[3]tetrathiafulvaleno[3]-paracyclophane is isolated by repeated recrystallization from cyclohexane. Melting point: 180°-182° C.

EXAMPLE 4

Preparation of [4]-tetrathiafulvaleno[4]paracyclophane (see formula IV):

p-Phenylene-δ,δ-divaleryl chloride 6.95 g (25 millimoles) of p-phenylene-δ,δ-divaleric acid are introduced into 70 ml of freshly distilled thionyl chloride. The mixture is refluxed for 2 hours at a bath temperature of 90° C. and the excess thionyl chloride is then removed on a rotary evaporator. A dark brown oil is left, which is stirred with cold petroleum ether (boiling range 40°-60° C.) until a black tarry product settles out round the edge (about 500 ml of petroleum ether are used). The petroleum ether solution is treated with active charcoal and then filtered. After concentrating the filtrate on a rotary evaporator, a pale brown product is left, which crystallizes in a refrigerator. Since the crystals deliquesce very rapidly when exposed to air, the material is not characterized and instead the crude product, which is obtained in a yield of 7.8 g (100%), is employed direct in the next reaction.

1,4-bis-(6'-Diazo-5'-oxohexyl)-benzene

The reaction is carried out behind a protective screen. 300 ml of a solution of diazomethane (about 0.25 mole) in ether are introduced into an Erlenmeyer flask equipped with a magnetic stirrer. A solution of 7.6 g (26.8 millimoles) of p-phenylene-δ,δ-divaleryl chloride in 100 ml of ether is slowly added dropwise, whilst cooling with ice. Gas is evolved. The mixture is left to stand for 24 hours and the ether and the excess diazomethane are then blown off with compressed air. The yellow solid residue is immediately employed in the next reaction step.

1,4-bis-(6'-Chloro-5'-oxohexyl)-benzene

A solution of about 27 millimoles of 1,4-bis-(6'-diazo-5'-oxohexyl)-benzene (prepared from 7.6 g of p-phenylene-δ,δ-divaleryl chloride) in 70 ml of methanol is added dropwise to a mixture of 58 ml of 5 M aqueous sodium chloride solution and 58 ml of 2 N aqueous hydrochloric acid solution. During the dropwise addition, the material in the reaction vessel must be cooled and stirred vigorously. After the addition, and when nitrogen evolution has ceased, stirring is continued for 4 hours at room temperature. 200 ml of water are added to the solution and the mixture is extracted with chloroform. The combined chloroform phases are washed with 200 ml of water and the pale yellow solution is dried over sodium sulfate. It is then filtered and concentrated on a rotary evaporator. The yellow solid residue is chromatographed on a silica gel column (length 50 cm, diameter 5 cm), using chloroform as the mobile phase. The bis-chloroketone migrates fastest. After concentrating the fractions, colorless 1,4-bis-(6'-chloro-5'-oxohexyl)-benzene is obtained, and this is recrystallized from cyclohexane. The substance is obtained in 53% yield (4.9 g); melting point 86°-87° C.

1,4-bis-(10'-Methyl-9'-oxa-5'-oxo-7'-thia-8'-thioxo-undecanyl)-benzene (see formula VII, with X=S, R=H and

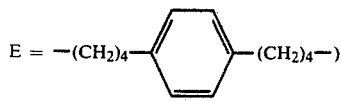

5.0 g (28.8 millimoles) of potassium isopropylxanthate are added to a solution of 4.5 g (13.1 millimoles) of 1,4-bis-(6'-chloro-5'-oxohexyl)-benzene in 150 ml of acetone, and the mixture is refluxed for 30 minutes, during which a colorless precipitate forms. The suspension is concentrated on a rotary evaporator and 200 ml of water are added to the residue. The mixture is extracted with chloroform and the organic phase is dried over sodium sulfate. It is concentrated on a rotary evaporator, to leave 12 g of a milky oil. This product is chromatographed over a silica gel column (length 50 cm, diameter 5 cm), using methylene chloride as the mobile phase. Colorless crystals are obtained and these are recrystallized from cyclohexane. The yield of 1,4-bis-(10'-methyl-9'-oxa-5'-oxo-7'-thia-8'-thioxo-undecanyl)-benzene is 5.3 g (75%). Melting point=114°-115° C.

1,4-bis-(4'-Isodithionylbutyl)-benzene (see formula VIII, with R=H, X=S and

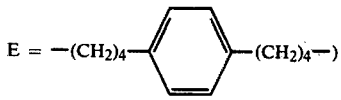

0.54 g (1 millimole) of 1,4-bis-(10'-methyl-9'-oxa-5'-oxo-7'-thia-8'-thioxo-undecanyl)-benzene is dissolved in a mixture consisting of 4 ml of ether and 4 ml of methylene chloride. 0.75 ml of perchloric acid is added dropwise, very slowly (over about 10 minutes), to the above solution, which is cooled by means of an ice bath. The mixture is then refluxed for 1.5 hours, on an oil bath at 40°-45° C. When the mixture has cooled, it is poured into ice water and the batch is stirred for 30 minutes. The two phases are then separated and the aqueous phase is washed once with methylene chloride. The combined organic phases are dried over sodium sulfate, filtered and concentrated on a rotary evaporator at 20° C. bath temperature. The colorless oil which remains is chromatographed over a silica bath column (length 30 cm, diameter 1 cm). The mobile phase used is a 1:1 mixture of carbon tetrachloride and chloroform. 1,4-bis-(4'-Isodithionylbutyl)-benzene is obtained as a semi-solid, colorless product in a yield of 276-330 mg (65-78%); this material can be employed, without further purification, in the subsequent reaction. For spectroscopic characterization of the product, a sample is separated on a preparative thin layer chromatography plate (silica gel), using a 1:1 mixture of carbon tetrachloride and chloroform as the mobile phase. Colorless crystals are obtained, which are triturated with ether and then filtered off. The melting point is 86°-88° C.

1,4-bis-(4'-Isotrithionylbutyl)-benzene (see formula IX, with R=H, X=S and

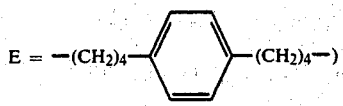

828 mg (1.96 millimoles) of 1,4-bis-(4'-isodithionyl-butyl)-benzene are dissolved in 30 ml of xylene and 1.74 g (3.92 millimoles) of phosphorus pentasulfide ($P_4S_{10}$) are then added. The mixture is refluxed for 2.5 hours on an oil bath at 140°-150° C. The reaction mixture turns reddish brown, after which a reddish brown precipitate settles out round the edge, leaving a deep yellow solution.

When the mixture has cooled, it is filtered, the residue is thoroughly washed with warm toluene, and the combined organic solutions are concentrated. A deep yellow oil remains, which is filtered over a Florisil column (length 30 cm, diameter 1 cm), using methylene chloride. After concentrating, a yellow crystalline product is obtained. This is chromatographed over a Florisil column (length 30 cm, diameter 1 cm), using a 7:3 mixture of carbon tetrachloride and chloroform as the mobile phase. 1,4-bis-(4'-Isotrithionylbutyl)-benzene is obtained in a yield of 431-530 mg (48-59%). Recrystallization from a small amount of toluene gives yellow crystals of melting point 104°-105° C.

1,4-bis-[4'-(2''-Methylthio-1'',3''-dithiol-4''-yl)-butyl]-benzene (see formula X, with R=H, X=S and

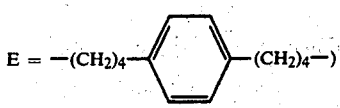

A solution of 837 mg (1.84 millimoles) of 1,4-bis-(4'-isotrithionylbutyl)-benzene in 5 ml of distilled nitromethane and 2 ml of distilled methyl iodide is refluxed for 2.5 hours on an oil bath at about 70° C. It is then allowed to cool, 1 ml of distilled methyl iodide is added and the mixture is stirred for 19 hours. During this time a precipitate forms and a very viscous paste results. A thin layer chromatogram (silica gel/methylene chloride) shows no residual starting compound. Since the bis-sulfonium iodide thus obtained decomposes when exposed to air and moisture, the solvent is blown off with nitrogen, the yellow precipitate is dried under reduced pressure from an oil pump and the product is employed without purification in the next reaction. Crude yield of bis-sulfonium iodide: 1.36 g (100%).

The crude bis-sulfonium iodide (1.36 g, 1.84 millimoles) is suspended in 10 ml of absolute tetrahydrofuran and 10 ml of absolute methanol and the suspension is cooled to −78° C. 700 mg (18.4 millimoles) of sodium tetrahydridoborate are added in 3 portions and the mixture is stirred for 3 hours at −78° C. The reaction mixture is then brought from −78° C. to −20° C. over 1.5 hours, after which it is poured into ether and the mixture is washed with water. The aqueous phase is washed twice with 50 ml of ether at a time and the combined ether solutions are washed twice with 100 ml of water at a time, and once with 100 ml of a saturated sodium chloride solution, and are then dried over sodium sulfate. After removing the solvent on a rotary evaporator, a reddish brown oil is obtained, which is chromatographed over a silica gel column (length 30 cm, diameter 1 cm), using methylene chloride as the mobile phase. A yellow oil is obtained in a yield of 852 mg (95%); this product is pure according to NMR spectroscopy.

bis-Dithiolium ion (see formula XI, with R=H, X=S and

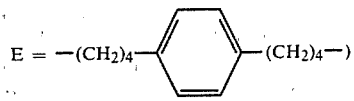

852 mg (1.75 millimoles) of 1,4-bis-[4'-(2''-methylthio-1'',3''-dithiol-4''-yl)-butyl]-benzene are emulsified in 12 ml of acetic anhydride under nitrogen and the emulsion is cooled to 0° C. 1.7 ml of a 48% strength aqueous solution of fluoboric acid is then added dropwise over a period of 10 minutes. A brown solution is obtained, which is stirred for 40 minutes at 0° C. During this time, a colorless precipitate forms. 40 ml of absolute ether are then added, thereby precipitating more of the product. The ether is pipetted off and the precipitate is washed four more times, in each case by adding 40 ml of absolute ether, stirring the reaction mixture and pipetting off the ether when the precipitate has settled out. After the last wash, the residual ether is blown off with nitrogen and the crude bis-dithiolium fluoborate is dried under reduced pressure from an oil pump. The pale brown precipitate is employed, without purification, in the next reaction.

[4]-Tetrathiafulvaleno[4]-paracyclophane

A solution of the crude bis-dithiolium fluoborate (992 mg, 1.75 millimoles) in 55 ml of absolute acetonitrile is slowly added dropwise (over 35 minutes) to a solution of 2 ml of absolute triethylamine in 20 ml of absolute acetonitrile at room temperature, under nitrogen. The mixture is then stirred for 40 minutes, after which the solvent is removed on a rotary evaporator. The residue is dried under reduced pressure from an oil pump and is then extracted with several portions of ether, until the ether phase no longer assumes a yellow color. The combined ether solutions are filtered through a Florisil column (length 30 cm, diameter 1 cm). After removing the solvent, brownish yellow crystals are obtained, which are redissolved in about 200 ml of absolute ether, this solution then being filtered over a silica gel column (length 30 cm, diameter 1 cm). After removing the solvent on a rotary evaporator and drying the residue under reduced pressure from an oil pump, [4]-tetrathiafulvaleno[4]-paracyclophane is obtained in the form of yellow crystals. The yield is 428 mg (63%) and the product is pure according to NMR spectroscopy.

For characterization, the compound is recrystallized from cyclohexane. Melting point=157°–158° C.

We claim:

1. A tetrathiafulvalenophane of the formula

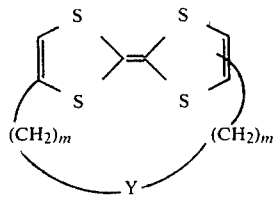

where m is 2, 3, 4 or 5 and Y is

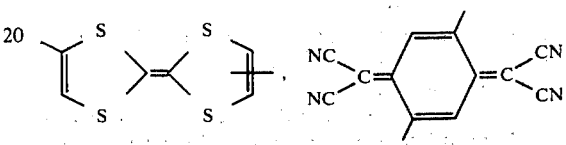

or p-phenylene which may contain cyano, nitro or halogen substituents.

2. A tetrathiafulvalenophane of the formula

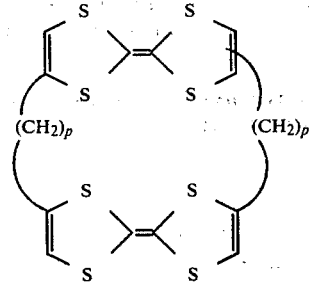

where p is 2, 3 or 4.

3. A tetrathiafulvalenoparacyclophane of the formula

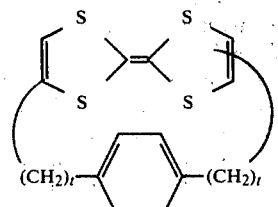

where t is 3, 4 or 5.

* * * * *